United States Patent [19]

Cross et al.

[11] 4,451,472
[45] May 29, 1984

[54] INHIBITION OF THROMBOXANE SYNTHETASE WITH 3-(HETEROALKYL)-INDOLYL-ACRYLIC ACID DERIVATIVES

[75] Inventors: Peter E. Cross, Canterbury; Roger P. Dickinson, Dover, both of England

[73] Assignee: Pfizer Inc., New York, N.Y.

[21] Appl. No.: 394,554

[22] Filed: Jul. 2, 1982

[30] Foreign Application Priority Data

Jul. 7, 1981 [GB] United Kingdom ............. 8120878
May 13, 1982 [GB] United Kingdom ............. 8213864

[51] Int. Cl.³ ................. A61K 31/415; C07D 403/06
[52] U.S. Cl. ........................... 424/263; 424/273 R; 546/273; 548/336
[58] Field of Search ................ 424/273 R, 263; 546/273; 548/336

[56] References Cited

U.S. PATENT DOCUMENTS 4,363,912 12/1982 Cross et al. ................. 546/273

FOREIGN PATENT DOCUMENTS 2024807 1/1980 United Kingdom .
2031408 4/1980 United Kingdom .
2025946 6/1980 United Kingdom .
2045244 10/1980 United Kingdom .

*Primary Examiner*—Jane T. Fan
*Attorney, Agent, or Firm*—Charles J. Knuth; Peter C. Richardson

[57] ABSTRACT

A series of novel 3-(1-imidazolylmethyl)indolylacrylic acid and 3-(3-pyridylmethyl)indolylacrylic acid derivatives has been prepared, including their pharmaceutically acceptable acid addition and base salts. These particular compounds are useful in therapy for the treatment of thrombosis, ischaemic heart disease, stroke, transient ischaemic attack, migraine, and the vascular complications of diabetes. Preferred member compounds include E-3-{1-[2-methyl-3-(1-imidazolylmethyl)]indolyl}-acrylic acid and E-3-{1-[2-methyl-3-(3-pyridylmethyl)]-indolyl} acrylic acid, respectively. Methods for preparing these compounds from known starting materials are provided.

15 Claims, No Drawings

INHIBITION OF THROMBOXANE SYNTHETASE WITH 3-(HETEROALKYL)-INDOLYL-ACRYLIC ACID DERIVATIVES

BACKGROUND OF THE INVENTION

This invention relates to certain novel indole derivatives and specifically, to certain new and useful 3-(1-imidazolylmethyl)indolylacrylic acid and 3-(3-pyridylmethyl)indolylacrylic acid derivatives. These particular compounds are able to selectively inhibit the action of the thromboxane synthetase enzyme without significantly inhibiting the action of the prostacyclin synthetase or cyclo-oxygenase enzymes. The compounds of the invention are therefore useful, for example, in the treatment of thrombosis, ischaemic heart disease, stroke, transient ischaemic attack, migraine, and the vascular complications of diabetes.

SUMMARY OF THE INVENTION

Thus, according to the invention, there are provided compounds of the general formula:

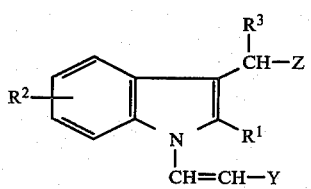

and the pharmaceutically acceptable acid addition and base salts thereof, wherein $R^1$ is hydrogen or alkyl of 1-4 carbon atoms; $R^2$ is hydrogen, alkyl of 1-4 carbon atoms, alkoxy of 1-4 carbon atoms or halogen; $R^3$ is hydrogen or methyl; Y is carboxy, carbalkoxy having 1-4 carbon atoms in the alkyl group or carboxamido; and Z is 1-imidazolyl or 3-pyridyl.

As used throughout this specification, the term "halogen" simply means fluorine, chlorine, bromine or iodine, while alkyl and alkoxy groups containing 3 or 4 carbon atoms may be either straight or branched chain.

More specifically, the preferred compounds of the invention are those in the E (trans) form, i.e., where the group "Y" is trans to the indole ring. In this connection, $R^3$ is preferably hydrogen, while $R^1$ and Y are preferably methyl and carboxy, respectively. $R^2$, on the other hand, is preferably hydrogen, methyl, methoxy or chlorine and when $R^2$ is other than hydrogen, the substituent is also preferably located at the 5-position of the molecule. In the most preferred series of compounds of the invention, $R^1$ is methyl, $R^2$ and $R^3$ are each hydrogen and Y is carboxy.

The invention also provides a pharmaceutical composition comprising a compound of the formula (I), or a pharmaceutically acceptable acid addition or base salt thereof, together with a pharmaceutically acceptable carrier or diluent.

The invention further provides a method of inhibiting the action of the thromboxane synthetase enzyme in an animal, including a human being, without significantly inhibiting the action of the prostacyclin synthetase or cyclo-oxygenase enzymes, which comprises administering to said animal an effective amount of a compound of the formula (I), or a pharmaceutically acceptable acid addition or base salt thereof, or a pharmaceutical composition comprising such a compound or salt together with a pharmaceutically acceptable carrier or diluent.

Pharmaceutically acceptable acid addition salts of the compounds of the invention are salts with acids containing pharmaceutically acceptable anions, e.g., the hydrochloride, hydrobromide, sulfate or bisulfate, phosphate or acid phosphate, acetate, maleate, fumarate, lactate, tartrate, citrate, gluconate, succinate and p-toluenesulfonate salts. Pharmaceutically acceptable base salts include the pharmaceutically acceptable metal and ammonium salts of those compounds where Y is carboxy and most preferably, they include the alkali metal salts.

Where the compounds of the invention contain an asymmetric center, the invention includes the racemic mixtures and the separated D- and L-optically active isomeric forms. These optically-active isomeric forms are, of course, readily obtainable by conventional methods, e.g., by fractional crystallization of a salt of the invention that is derived from a suitably selected optically-active acid (e.g., tartaric acid).

DETAILED DESCRIPTION OF THE INVENTION

The compounds of the invention may be prepared by a number of different routes, including the following:

(1) The compounds of the formula (I) can be prepared by the following reaction scheme:

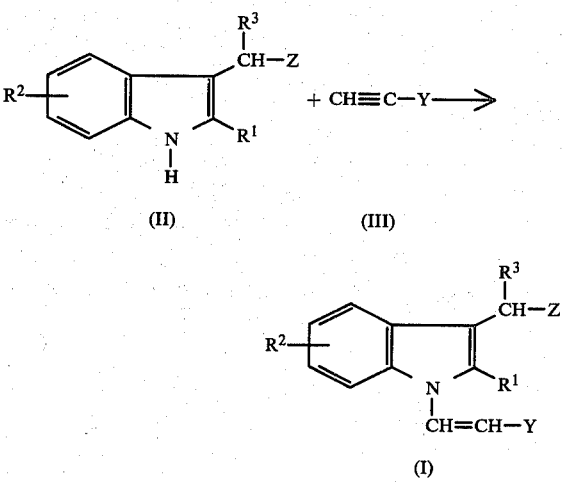

wherein $R^1$, $R_2$, $R_3$, Y and Z are each as previously defined for the aforesaid structural formula. In a typical procedure, the iodole starting material (II) and the alkylene reagent (III) are reacted together in a suitable organic solvent, such as dioxane or tetrahydrofuran, preferably in the presence of a base like benzyltrimethylammonium hydroxide or tetrabutylammonium fluoride, for a period of approximately up to four hours, generally at room temperature ($\sim 20°$ C.), although the reaction mixture may also be heated to a temperature of up to about 100° C. in order to accelerate the rate of the reaction. The desired product can then be isolated and purified by conventional procedures as hereinafter illustrated in the various Examples of the instant specification.

It is to be noted that this particular route always affords the products in the E-form, i.e., where the group "Y" is trans to the indole ring. Products in the Z (cis) form are obtainable by irradiation of the E-form product with ultraviolet light in accordance with conventional physical-chemical procedures.

The starting materials of the formulae (II) and (III) are either known compounds or else they can easily be prepared by using procedures analogous to those described in the prior art. For instance, the starting materials in which Z is 1-imidazolyl are all described in European Pat. No. 3,901. On the other hand, the starting materials in which Z is 3-pyridyl can easily be prepared by using the following routes, viz.,

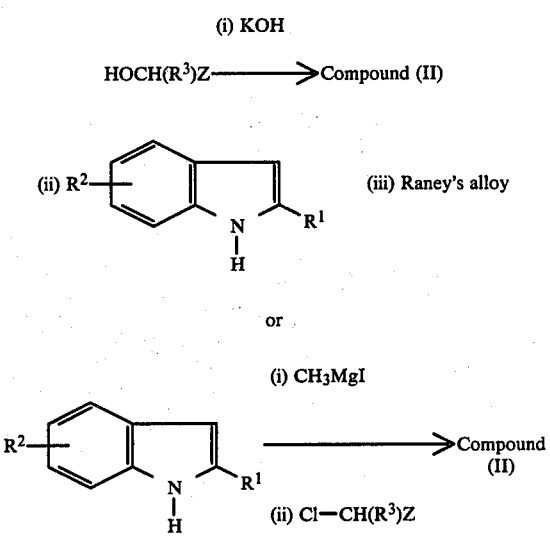

The starting indoles mentioned above are already described in European Pat. No. 3,901.

Pyridyl intermediates of the formula (II) in which $R^3$ is methyl and Z is 3-pyridyl, and $R^1$, $R^2$ and $R^3$ are all as previously defined for structural formula (I) can also be prepared in the following manner:

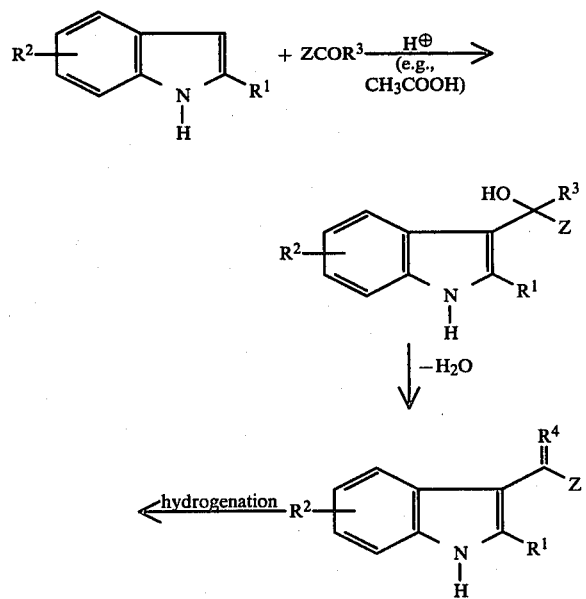

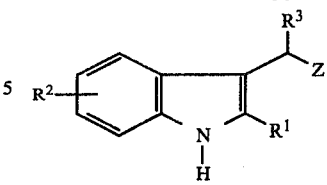

wherein $R^4$ is the alkylene group having the same number of carbon atoms as $R^3$. For example, the dehydration of the compound in which $R^3$ is methyl yields the compound in which $R^4$ is methylene, which compound is then hydrogenated to the desired end product using standard procedure (e.g., catalytic hydrogenation in ethanol over Pd/C at 2–5 atm.).

(2) Certain of the groups in the definition of Y in structural formula (I) can also be obtained by means of chemical transformation reactions as will be well known to those skilled in the art. For instance, compounds of the formula (I) wherein Y is a carboxy group can easily be obtained from the corresponding esters wherein Y is a carbalkoxy group as previously defined, using standard chemical hydrolytic reactions and preferably, by such means as alkaline hydrolysis. The acid compound so obtained may then be converted to a variety of derivatives, e.g., formation of the acid chloride or bromide or the imidazolide, followed by reaction with ammonia then gives the corresponding amides where Y is $CONH_2$. In like manner, the esters in which Y is carbalkoxy (as previously defined) can also be reacted with ammonia to yield the corresponding amides.

All these reactions are entirely conventional and the methods and conditions for their performance will be well known to those skilled in the art, as is the case with other possibilities and variations.

The pharmaceutically acceptable acid addition salts of the compounds of the invention can be prepared by conventional procedures, e.g., by reacting a solution of the free base in a suitable solvent, e.g., ethanol, with a solution containing at least one equivalent of the appropriate mineral or organic acid in a suitable solvent such as diethyl ether. The desired acid addition salt generally precipitates from solution is else is recovered by means of evaporation of the solvent. In like manner, the pharmaceutically acceptable metal and ammonium salts can also be prepared by employing conventional procedures.

The compounds of the invention of formula (I) and their pharmaceutically acceptable salts have been found to selectively inhibit the action of the thromboxane synthetase enzyme without significantly affecting the action of the prostacyclin synthetase or cyclo-oxygenase enzymes. Thus, the compounds are of value in the treatment of a wide variety of clinical conditions which are characterized by an imbalance of prostacyclin/thromboxane $A_2$, including thrombosis, ischaemic heart disease, stroke, transient ischaemic attack, migraine, and the vascular complications of diabetes, as hereinafter explained below.

For instance, research work has established that in most tissues the major product of the arachidonic acid metabolism is either of two unstable substances, viz, thromboxane $A_2$ ($TxA_2$) or prostacyclin ($PGI_2$) (Proc. Nat. Acad. Sci. U.S.A., 1975, 72, 2994; Nature, 1976, 263, 663; Prostaglandins, 1976, 12, 897). In most cases, the prostaglandins $PGE_2$ and $PGD_2$ are comparatively minor by-products in this particular bio-synthetic pathway. The discovery of thromboxane $A_2$ and prostacyclin has significantly increased our understanding of vascular homeostasis. Prostacyclin, for example, is a powerful vasodilator and inhibitor of platelet aggregation, and in this last respect, it is the most potent endogenous substance so far discovered. The prostacyclin synthetase enzyme is located in the endothelial layer of the vasculature and is fed by endoperoxides released by blood platelets coming into contact with the vessel wall. The prostacyclin thus produced is important for prevention of platelet deposition on vessel walls (Prostaglandins, 1976, 12, 685; Science, 1976, 17; Nature 1978, 273, 765).

Thromboxane $A_2$, on the other hand, is synthesized by the thromboxane synthetase enzyme which is located in, for example, the blood platelets. Thromboxane $A_2$ is a powerful vasoconstrictor and pro-aggregatory substance. As such, its actions are in direct opposition to those of prostacyclin. If, for any reason, prostacyclin formation by the vasculature is impaired, then the endoperoxides produced by platelets coming into contact with the vessel wall are converted into thromboxane, but are not converted effectively into prostacyclin (Lancet, 1977, 18; Prostaglandins, 1978, 13, 3). Alteration of the prostacyclin/thromboxane balance in favor of the latter substance could result in platelet aggregation, vasospasm (Lancet, 1977, 479; Science, 1976, 1135; Amer. J. Cardiology, 1978, 41, 787) and an increased susceptibility to artherothrombosis (Lancet, (i), 1977, 1216).

It is also known that in experimental artherosclerosis, prostacyclin generation is suppressed and thromboxane $A_2$ production is enhanced (Prostaglandins, 1977, 14, 1025 and 1035). Thus, thromboxane $A_2$ has been implicated as the causative agent in variant angina, myocardial infarction, sudden cardiac death and stroke (Thromb. Haemostasis, 1977, 38, 132). Studies in rabbits have shown that electrocardiogram (ECG) changes typical of these conditions were produced when freshly prepared thromboxane $A_2$ was injected directly into the animal's heart (N, Kharasch and J. Fried (Editors), "Biochemical Aspects of the Prostaglandins and Thromboxanes," Academic Press, Inc., New York, 1977, p. 189). This technique is considered to represent a unique animal model of the heart attacks of coronary patients and has been used to show that administration of a compound believed to antagonize the effects of thromboxane $A_2$ protects the rabbits from the adverse consequences of thromboxane $A_2$ injection.

Another area where a $PGI_2/TxA_2$ imbalance is considered to be a contributory factor is that of migraine. The migraine headache is associated with changes in intra- and extra-cerebral blood flow and in particular, it involves a pre-headache reduction of cerebral blood flow followed by dilation in both vascular areas during the headache phase. Prior to the development of the headache, blood levels of 5-hydroxytryptamine are elevated and this suggests the occurrence of in vivo aggregation and release of the amine from the platelet stores. It is known that the blood platelets of migraine patients are more prone to aggregate than are those of normal individuals (J. Clin. Pathol., 1971, 24, 250; J. Headache, 1977, 17, 101). Furthermore, it has now been postulated that not only is an abnormality of platelet function a major factor in the pathogenesis of migraine attacks, but it is also, in fact, their prime cause (Lancet, (i), 1978, 501). Thus, a drug that selectively modified platelet function to inhibit thromboxane $A_2$ formation would have to be of considerable benefit in migraine therapy.

Abnormalities of platelet behavior have been reported in patients with diabetes mellitus (Metabolism, 1979, 28, 394; Lancet, 1978 (i) 235). Diabetic patients are known to be particularly susceptible to microvascular complications, atherosclerosis and thrombosis and platelet hyper-reactivity has been suggested as the cause of such angiopathy. Diabetic platelets produce elevated amounts of $TxB_2$ and malondialdehyde (Symposium "Diabetes and Thrombosis—Implications for Therapy," Leeds, U.K., April 1979). Also, it has been shown that in rats with experimental diabetes vascular prostacyclin production is impaired and $TxA_2$ synthesis from the platelets is elevated (IV International Prostaglandin Conference, Washington, D.C. May, 1979). Thus, the imbalance between prostagcyclin and $TxA_2$ is considered to be responsible for the microvascular complications of diabetes. A $TxA_2$-synthetase inhibitor could therefore find clinical utility in preventing these vascular complications.

Aspirin and most other non-steroidal antiinflammatory (NSAI) drugs inhibit the cyclo-oxygenase enzyme. The effect of this action is to shut down the production of the $PGG_2/H_2$ endoperoxides and by so doing, to reduce both the prostacyclin and thromboxane $A_2$ levels. Aspirin and aspirin-like drugs have been evaluated clinically for the prevention of stroke and heart attack (New England J. Med., 1978, 299, 53; Brit. Med. J., 1978, 1188; Stroke, 1977, 8, 301). Although some encouraging results have been obtained with these drugs, a compound which specifically inhibits thromboxane $A_2$ formation while leaving the biosynthesis of prostacyclin unimpaired would, of course, necessarily be more valuable in these same clinical conditions (Lancet, (ii), 1978, 780).

The effect of the compounds of the formula (I) on the thromboxane synthetase enzyme, and the prostacyclin synthetase and cyclo-oxygenase enzymes has been measured by the following in vitro enzyme assay tests:

1. Cyclo-oxygenase

Ram seminal vesicle microsomes (Biochemistry, 1971, 10, 2372) are incubated with arachidonic acid (100 $\mu$M) at 22° C. for a period of one minute so as to produce $PGH_2$, and aliquots of this reaction mixture injected into a stream of Krebs-bicarbonate at 37° C. [containing a mixture of antagonists (Nature, 1978, 218, 1135) and indomethacin (Brit. J. Pharmacol., 1972, 45, 451)] which is superfusing a spirally-cut rabbit aorta strip (Nature, 1969, 223, 29). The ability of compound to inhibit the enzyme is measured by comparing the increases in isomeric tension produced by $PGH_2$ in the absence of the test compound and again, following pre-incubation of the enzyme with the test compound for a period of five minutes (Agents and Actions, 1981, 11, 274).

2. Prostacyclin $PGI_2$) Synthetase

Pig aorta microsomes (Nature, 1976, 263, 663) are incubated with $PGH_2$ (produced as in assay test No. 1) at 22° C. for a period of 30 seconds and aliquots are then bio-assayed in the same manner as hereinbefore described. $PGI_2$ production is assessed indirectly by measuring the decrease in $PGH_2$-induced tension ($PGI_2$ itself does not contract the aorta). This decrease in tension can be prevented completely by pre-incubation of the enzyme with the selective $PGI_2$ synthetase inhibitor, known chemically as 15-hydroperoxy-arachidonic acid (Prostaglandins, 1976, 12, 715). The test compound is then pre-incubated with the enzyme for a period of five minutes and its ability to prevent the decrease in tension is subsequently measured.

3. Thromboxane $A_2$ ($TxA_2$) Synthetase

Indomethacin-pretreated human platelet microsomes (Science, 1976, 193, 163) are incubated with $PGH_2$ (produced as described in test No. 1) at 0° C. for a period of two minutes, and aliquots of the reaction mixture are then superfused over two rabbit aorta spirals which are separated by a delay coil (2 min.). The latter is required in order to allow for the selective decay of the more unstable thromboxane $A_2$ (Proc. Nat. Acad. Sci., 1975, 72, 2994), thereby enabling separate measurement of the increased isometric tension due to the $TxA_2$ formed and the $PGH_2$ remaining to take place. The test compound is then pre-incubated with the enzyme for a period of five minutes, and its ability to inhibit the thromboxane synthetase enzyme is measured as its reduction of the $TxA_2$ component of the isometric tension.

Compounds of the invention, when tested in this way, have been shown to be capable of selectively inhibiting the thromboxane synthetase enzyme.

In addition to the above, an in vitro assay test for measuring the inhibition of human blood platelet aggregation has been described and this may be considered predictive of anti-thrombotic efficacy from a clinical point of view (e.g., see Lancet, (ii), 1974, 1223 and J. Exp. Med., 1967, 126, 171). For example, both the clinically-effective agents known as aspirin and sulphinpyrazone, respectively, show inhibitory activity in vitro against a variety of aggregating agents employed in this test.

A number of in vivo tests in animals have also been described for evaluating potential anti-thrombotic drugs. For instance, the method of Patrono et al. is adapted to study the generation of $TxB_2$ in whole blood samples removed from animals prior to and following drug treatment. Briefly, blood samples are taken into glass tubes and allowed to clot at 37° C. Serum is then separated by centrifugation and the samples stored at $-40°$ C. until assayed for $TxB_2$, when appropriate dilutions of ethanol deproteinized samples are thereafter analyzed by RIA. This technique is used in experiments with the test compounds to determine intravenous potency in anesthetized rabbits.

In this study, male New Zealand white rabbits (2.6–5.6 kg.) are anesthetized with sodium pentobarbitone (30 mg./kg., i.v.), followed by urethane (500 mg./kg., i.p.). After cannulation of the trachea, a carotid artery is catheterized for collection of the blood samples. The catheter is kept patent by slow infusion (0.2 ml./minutes) of sterile saline. Control carotid arterial blood samples are then taken at 30 minutes and at 5 minutes prior to administration of the test compound or vehicle (0.9% w./v. NaCl, 0.2 ml./kg.) via a marginal ear vein. Three groups of rabbits are employed in the test. The first group is given the test compound at 0.03 mg./kg., followed one hour later by a second dose at 0.1 mg./kg. Similarly, the second group is administered the test compound at 0.3 mg./kg., followed by a second dose (one hour later) at 1.0 mg./kg. The third group is treated with the vehicle alone, followed one hour later by a further vehicle injection. Carotid arterial blood samples are then taken at various time intervals after all doses. At each time point, a 1.0 ml. blood sample is taken into a glass tube, without anticoagulant, for $TxB_2$ determination. For the latter determination, the blood sample is allowed to clot during a two-hour incubation period at 37° C. (which preliminary experiments had already shown to give a maximum $TxB_2$ production) and the resulting serum obtained by centrifugation. The serum samples are then processed through the $TxB_2$-RIA after deproteinization with ethanol and dilution with Isogel Tris buffer.

Thus, it has been shown that intravenous injection of arachidonic acid in rabbits causes death by platelet clumping and embolization in the lungs. Again, both the clinically-effective aspirin (Agents and Actions, 1977, 1, 481) and sulphinpyrazone (Pharmacology, 1976, 14, 522) protect the rabbit from the lethal effect of the injection. Sulphinpyrazone has also been shown to prevent the aggregation of platelets in an extra corporeal loop of the abdominal aorta of rats in vivo (Throm. Diathes. Haemostasis, 1973, 30, 138).

Again, the compounds of the present invention are considered to be effective inhibitors of human blood platelet aggregation when subjected to the above (in vitro and in vivo) assay procedures, in addition to being useful in protecting rabbits against the lethal effect of arachidonic acid injection and in preventing the aggregation of blood platelets in the rat aorta.

The compounds can be administered orally in the form of tablets or capsules containing a unit dose of the compound together with such excipients as corn starch, calcium carbonate, dicalcium phosphate, alginic acid, lactose, magnesium stearate and talc. The tablets are typically prepared by granulating the ingredients together and compressing the resulting mixture into tablets of the desired size. The capsules are typically prepared by granulating the ingredients together and filling them into hard gelatin capsules of the appropriate size to contain the proper ingredients.

The compounds can also be administered parenterally, for example, by intramuscular, intravenous or subcutaneous injection, or by infusion of a parenteral solution of same into a vein. For parenteral administration, in general, they are best used in the form of a sterile aqueous solution which may also contain other solutes such as tonic and pH adjusters. The compounds may, e.g., be added to distilled water and the pH subsequently adjusted to a value in the range of pH 3–6 with the aid of an acid such as citric acid, lactic acid or hydrochloric acid, etc. A sufficient amount of other solutes such as dextrose or saline may then be added to the mixture to render the final solution isotonic. The resulting solution is then sterilized according to the method of British Pharmacopoeia, 1973, by filtration through a bacteria-proof filter under aseptic conditions into sterile containers, so as to comply with the test for sterility of Appendix 121 in British Pharmacopoeia, 1973. Suitable containers for these purposes include, for example, sterile glass vials of an appropriate size to contain the desired volume of solution, which volume will typically contain a unit dose of the compound of the formula (I).

For oral administration to human patients, the daily dosage level of a compound to be administered will be from about 0.1 to 20 mg./kg. per day for a typical adult patient (70 kg.). For parenteral administration, the daily dosage level of a compound of the formula (I) will be from about 0.01–0.5 mg./kg. per day, for a typical adult patient. Thus, tablets or capsules can generally be expected to contain anywhere from approximately 5 to 150 mg. of the active compound for administration orally up to three times a day, while dosage units for parenteral administration can be expected to contain roughly from 0.5–35 mg. of the active compound on this basis. A typical vial used in the latter connection would be a 10 ml. vial containing 5 mg. of the active compound made up in 6–10 ml. of sterile solution.

It will, of course, be appreciated that the physician will, in any event, determine the actual dosage to be employed for the present purposes at hand and that this will be the dosage which is most suitable for the individual and it will vary with the age, weight and response of the patient. The above dosages are merely exemplary of the average host. There may, of course, be individual cases where higher or lower dosages are clearly called for, i.e., dosages which are above or below the limits set by the aforementioned ranges.

PREPARATION A

3-Pyridylmethanol (27.25 g.) was added to a suspension of potassium hydroxide (2.24 g.) in xylene (200 ml.) and the resulting mixture was heated at reflux, using a Dean and Stark apparatus to remove the water. Upon cooling, 2-methylindole (16.4 g.) was added thereto and the resulting mixture was heated at reflux for a period of three hours. Raney alloy (1.0 g.) was then added to the hot solution and heating at reflux was continued overnight (a period of approximately 16 hours). Upon completion of this step, the spent reaction mixture was cooled to room temperature ($\sim 20°$ C.) and the metallic residue was removed therefrom by means of filtration and thereafter washed with diethyl ether (25 ml.). The combined organic filtrate was next extracted with water (two-100 ml. portions), and the resulting organic layer was subsequently separated and cooled to 0° C. At this point, a solid precipitate formed and the latter material was subsequently recovered from the mixture by means of suction filtration and then crystallized from toluene to afford pure 2-methyl-3-(3-pyridylmethyl)indole (yield, 14.6 g.), m.p. 207°–210° C.

Anal. Calcd. for $C_{15}H_{14}N_2$: C, 80.6; H, 6.3; N, 12.15. Found C, 81.05; H, 6.35; N, 12.6.

PREPARATION B

A solution consisting of 1-(2-methyl-3-indolyl)-1-(3-pyridyl)ethylene (9.37 g.), prepared according to the procedure described in the *Journal of Heterocyclic Chemistry*, Vol. 9, p. 833 (1972), dissolved in ethanol (200 ml.) was hydrogenated at 2.5 atmospheric pressure in the presence of 10% palladium-on-charcoal catalyst. The resulting reaction mixture was then filtered to remove the catalyst and the filtrate subsequently evaporated under reduced pressure to afford a residue. Crystallization of the latter material from an ethyl acetate/petroleum ether (b.p. 60°–80° C.) mixture then gave pure 2-methyl-3-[1-(3-pyridyl)ethyl]indole (yield, 5.74 g.), m.p. 139°–141° C.

Anal. Calcd. for $C_{16}H_{16}N_2$: C, 81.32; H, 6.83; N, 11.86. Found: C, 81.56; H, 7.11; N, 11.65.

EXAMPLE 1

Ethyl propiolate (540 mg.) was added dropwise to a stirred solution consisting of 2-methyl-3-(1-imidazolylmethyl)indole (1.05 g.), prepared according to European Pat. No. 3,901, and benzyltrimethylammonium hydroxide (0.5 ml. of 40% solution in methanol) dissolved in dioxane (12 ml.), and the resulting mixture was stirred at room temperature ($\sim 20°$ C.) for a period of two hours. At the end of this time, the spent reaction mixture was evaporated to dryness while under reduced pressure and the resulting residue was thereafter poured into water and subsequently extracted several times with ethyl acetate. The combined organic extracts were next washed with water and subsequently dried over anhydrous sodium sulfate. After removal of the drying agent by means of filtration and the solvent by means of evaporation under reduced pressure, there was finally obtained an oil which was subsequently chromatographed on silica gel. Elution with chloroform then gave an oil (1.1 g.) which was later shown by nuclear magnetic resonance (n.m.r.) data to be a mixture of the methyl and ethyl esters of the desired product.

The ester mixture (800 mg.) obtained above was then dissolved in ethanol (2.0 ml.) and a solution of sodium hydroxide (210 mg.) in water (20 ml.) was added thereto. The resulting mixture was then heated on a steam bath for a period of six hours and finally evaporated to dryness while under reduced pressure. The residue was then dissolved in a small volume of water and the resulting aqueous solution was subsequently acidified with glacial acetic acid to yield a precipitate. The latter material was then collected by means of suction filtration, washed with water and subsequently crystallized from isopropanol to ultimately afford pure E-3-{1-[2-methyl-3-(1-imidazolyl-methyl)]indolyl}-acrylic acid (yield, 320 mg.), m.p. 228°–230° C.

Anal. Calcd. for $C_{16}H_{15}N_3O_2$: C, 68.31; H, 5.38; N, 14.94. Found: C, 68.28; H, 5.48; N, 14.60.

EXAMPLE 2

The procedure described in Example 1 was repeated except that 2-methyl-3-(3-pyridylmethyl)indole (the product of Preparation A) was the starting material employed in place of 2-methyl-3-(1-imidazolylmethyl)indole, using the same molar proportions as before. In this particular case, the corresponding final product obtained after hydrolysis of the intermediate ester was E-3-{1-[2-methyl-3-(3-pyridylmethyl)]indolyl}-acrylic acid, m.p. 206°–207° C. after recrystallization from methanol.

Anal. Calcd. for $C_{18}H_{16}N_2O_2$: C, 73.95; N, 5.52; N, 9.58. Found: C, 73.48; H, 5,53; N, 9.78.

EXAMPLE 3

A 1 M solution of tetrabutylammonium fluoride in tetrahydrofuran (50 ml.) was added dropwise to a stirred solution consisting of 2-methyl-3-(1-imidazolylmethyl)indole (10.55 g.) and ethyl propiolate (4.90 g.) dissolved in dry tetrahydrofuran (150 ml.) at room temperature ($\sim 20°$ C.). The resulting mixture was then stirred at room temperature for a period of two hours and finally poured into water. The aqueous mixture so obtained was next extracted several times with ethyl acetate and the combined organic extracts were subsequently washed well with water and dried over anhydrous sodium sulfate. After removal of the drying agent by means of filtration and the solvent by means of evaporation under reduced pressure, there was obtained a solid residue which was subsequently chromatographed on silica gel. Elution with chloroform then gave some impurity initially, followed by the pure product in later fractions. Subsequent evaporation of the product-containing fractions then gave a solid material, which later crystallized from a chloroform/petroleum ether (b.p. 40°–60° C.) mixture to ultimately afford pure E-3-{1-[2-methyl-3-(1-imidazolylmethyl)]indolyl} acrylic acid ethyl ester (yield, 8.00 g.), m.p. 121°–122° C.

Anal. Calcd. for $C_{18}H_{18}N_3O_2$: C, 69.88; H, 6.59; N, 13.58. Found: C, 69.69; H, 6.16; N, 13.57.

EXAMPLE 4

The procedure described in Example 3 was repeated except that 5-methoxy-3-(1-imidazolylmethyl)indole (European Patent No. 3,901) was the starting material employed in place of 2-methyl-3-(1-imidazolylmethyl)indole, using the same molar proportions as before. In this particular case, the corresponding final product obtained was E-3-{1-[5methoxy-3-(1imidazolylmethyl)-]indolyl} acrylic acid ethyl ester, m.p. 115°–116° C.

Anal. Calcd. for $C_{18}H_{19}N_3O_3$: C, 66.44; H, 5.89; N, 12.92. Found: C, 66.48; H, 5.92; N, 12.57.

EXAMPLE 5

The procedure described in Example 3 was repeated except that 2,5-dimethyl-3-(3-pyridylmethyl)indole was the starting material employed in place of 2-methyl-3-(1-imidazolylmethyl)indole, using the same proportions as before. In this particular case, the corresponding final product obtained was E-3-{1-[2,5-dimethyl-3-(3-pyridylmethyl)]indolyl} acrylic acid ethyl ester, m.p. 125°–126° C.

Anal. Calcd. for $C_{21}H_{22}N_2O_2$: C, 75.42; H, 6.63; N, 8.38. Found: C, 75.20; H, 6.43; N, 8.34.

EXAMPLE 6

The procedure described in Example 3 was repeated except that 5-chloro-2-methyl-3-(3-pyridylmethyl)indole was the starting material employed in place of 2-methyl-3-(1-imidazolylmethyl)indole, using the same molar proportions as before. In this particular case, the corresponding final product obtained was E-3-{1-[5-chloro-2-methyl-3-(3-pyridylmethyl)]indolyl} acrylic acid ethyl ester, m.p. 126°–127° C.

Anal. Calcd. for $C_{20}H_{19}ClN_2O_2$: C, 67.69; H, 5.40; N, 7.90. Found: C, 67.55; H, 5.38; N, 8.03.

EXAMPLE 7

The procedure described in Example 3 was repeated except that 2-methyl-3-[1-(3-pyridyl)ethyl]indole (the product of Preparation B) was the starting material employed in place of 2-methyl-3-(1-imidazolylmethyl)indole, using the same molar proportions as before. In this particular case, the corresponding final product obtained was E-3-{{1-{2-methyl-3-[1-(3-pyridyl)ethyl]} indolyl}} acrylic acid ethyl ester. The product hydrolyzed directly after chromatography.

EXAMPLE 8

The procedure described in Example 1 to hydrolyze the ethyl ester of E-3-{1-[2-methyl-3-(1-imidazolylmethyl)]indolyl} acrylic acid (see second paragraph) was repeated except that E-3-{1-[5-methoxy-3-(1-imidazolylmethyl)]indolyl} acrylic acid ethyl ester (the product of Example 4) was the starting material employed in place of the previously mentioned compound, using the same molar proportions as before. In this particular case, the corresponding final product obtained was E-3-{1-[5-methoxy-3-(1imidazolylmethyl)-]indolyl} acrylic acid, m.p. 223°–224° C.

Anal. Calcd. for $C_{16}H_{15}N_3O_3$: C, 64.63; H, 5.09; N, 14.14. Found: C, 64.84; H, 5.10; N, 14.14.

EXAMPLE 9

The procedure described in Example 1 to hydrolyze the ethyl ester of E-3-{1-[2-methyl-3-(1-imidazolylmethyl)]indolyl} acrylic acid was repeated except that E-3-{1-[2,5-dimethyl-3-(3-pyridylmethyl)]indolyl}acrylic acid ethyl ester (the product of Example 5) was the starting material employed in place of the previously mentioned compound, using the same molar proportions as before. In this particular case, the corresponding final product obtained was E-3-{1-[2,5-dimethyl-3-(3-pyridylmethyl)]indolyl} acrylic acid, m.p. 238°–240° C.

Anal. Calcd. for $C_{19}H_{18}N_2O_2$: C, 74.49; H, 5.92; N, 9.15. Found: C, 74.28; H, 6.00; N, 8.92.

EXAMPLE 10

The procedure described in Example 1 to hydrolyze the ethyl ester of E-3-{1-[2-methyl-3-(1-imidazolylmethyl)]indolyl} acrylic acid was repeated except that E-3-{1-[5-chloro-2-methyl-3-(3-pyridylmethyl)]indolyl} acrylic acid ethyl ester (the product of Example 6) was the starting material employed in place of the previously mentioned compound, using the same molar proportions as before. In this particular, case, the corresponding final product obtained was E-3-{1-[5-chloro-2-methyl-3-(3-pyridylmethyl)]indolyl} acrylic acid, m.p. 242°–243° C.

Anal. Calcd. for $C_{18}H_{15}ClN_2O_2$: C, 66.15; H, 4.63; N, 8.51. Found: C, 65.75; H, 4.34; N, 8.46.

EXAMPLE 11

The procedure described in Example 1 to hydrolyze the ethyl ester of E-3-{1-[2-methyl-3-(1-imidazolylmethyl)]indolyl} acrylic acid was repeated except that E-3-{{1-{2-methyl-3-[1-(3-pyridyl)ethyl]} indolyl}}acrylic acid ethyl ester (the product of Example 7) was the starting material employed in place of the previously mentioned compound, using the same molar proportions as before. In this particular case, the corresponding final product obtained was E-3-{{1-{2-methyl-3-[1-(3-pyridyl)ethyl]} indolyl}} acrylic acid, m.p. 188°–189° C.

Anal. Calcd. for $C_{19}H_{18}N_2O_2$: C, 74.49; H, 5.92; N, 9.15. Found: C, 74.32; H, 6.21; N, 8.83.

EXAMPLE 12

A mixture consisting of E-3-{1-[5-chloro-2-methyl-3-(3-pyridylmethyl)]indolyl} acrylic acid (330 mg.), the product of Example 10, and N,N'-carbonyldiimidazole (200 mg.) in dry dioxane (5.0 ml.) was heated on a steam bath for a period of two hours and then evaporated. To the resulting residue, there was then added an excess of a concentrated alcoholic solution of ammonia in ethanol and the organic solution so obtained was then allowed to stand at room temperature (~20° C.) for a period of 30 minutes and finally evaporated to dryness while under reduced pressure. The gummy residue which resulted was then triturated with water to give a solid, which was subsequently crystallized from methanol to ultimately yield pure E-3-{1-[5-chloro-2-methyl-3-(3-pyridylmethyl)]indolyl}acrylamide, m.p. 262°–263° C.

Anal. Calcd. for $C_{18}H_{16}ClN_3O$: C, 66.36; H, 4.95; N, 12.90. Found: C, 65.88; H, 5.23; N, 12.44.

EXAMPLE 13

The following compounds were tested in groups of anaesthetized male New Zealand while rabbits (average weight, 2.6–5.6 kg.) for anti-thrombotic activity according to the procedure previously described at the different dose levels indicated and the results obtained are reported in the table below where the percent inhibition of thromboxane B₂(TxB₂) formation after intravenous administration to said animals is recorded at the 2-, 15-, 30-, 45- and 75-minute time intervals, respectively:

| Compound | Dose (mg/kg) | Percent Inhibition (%) | | | | |
|---|---|---|---|---|---|---|
| | | 2 | 15 | 30 | 45 | 75 MIN. |
| Product of Ex. 1 | 0.3 | — | 93 | 93 | — | — |
| Product of Ex. 1 | 1.0 | 93 | 96 | — | 95 | 95 |
| Product of Ex. 2 | 0.1 | — | 81 | 82 | — | — |
| Product of Ex. 2 | 0.3 | 95 | 98 | — | 93 | 90 |
| Product of Ex. 2 | 1.0 | 97 | 94 | — | 97 | 95 |

We claim:

1. A compound of the formula:

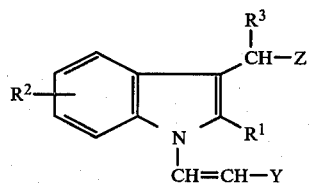

or a pharmaceutically acceptable acid addition or base salt thereof, wherein $R^1$ is hydrogen or alkyl of 1–4 carbon atoms;
$R^2$ is hydrogen, alkyl of 1–4 carbon atoms, alkoxy of 1–4 carbon atoms or halogen;
$R^3$ is hydrogen or methyl;
Y is carboxy, carbalkoxy having 1–4 carbon atoms in the alkyl group or carboxamido; and
Z is 1-imidazolyl or 3-pyridyl.

2. A compound as claimed in claim 1 which is in the Z form wherein the Y group is cis to the indole ring.

3. A compound as claimed in claim 1 which is in the E form wherein the Y group is trans to the indole ring.

4. A compound as claimed in claim 3 wherein $R_3$ is hydrogen.

5. A compound as claimed in claim 3 wherein $R^1$ is methyl and Y is carboxy.

6. A compound as claimed in claim 3 wherein $R^1$ is methyl, $R^3$ is hydrogen and Y is carboxy.

7. A compound as claimed in claim 3 wherein $R^1$ is methyl, $R^2$ and $R^3$ are each hydrogen and Y is carboxy.

8. E-3-{1-[2-Methyl-3-(1-imidazolylmethyl)]indolyl} acrylic acid.

9. E-3-{1-[2-Methyl-3-(3-pyridylmethyl)]indolyl} acrylic acid.

10. A pharmaceutical composition useful for inhibiting the action of the thromboxane synthetase enzyme in an animal without significantly inhibiting the action of the prostacyclin synthetase or cyclo-oxygenase enzymes, said composition comprising a pharmaceutically acceptable carrier and a therapeutically-effective amount of a compound as claimed in claim 1.

11. The composition according to claim 10 wherein the compound is E-3-{1-[2-methyl-3-(1imidazolylmethyl)]indolyl} acrylic acid.

12. The composition according to claim 10 wherein the compound is E-3-{1-[2-methyl-3-(3-pyridylmethyl)]indolyl} acrylic acid.

13. A method for inhibiting the action of the thromboxane synthetase enzyme in an animal without significantly inhibiting the action of the protascyclin synthetase or cyclo-oxygenase enzymes, which comprises administering to said animal a thromboxane synthetase enzyme inhibiting amount of a compound as claimed in claim 1.

14. The method as claimed in claim 13 wherein said compound is E-3-{1-[2-methyl-3-(1-imidazolylmethyl)]indolyl} acrylic acid.

15. The method as claimed in claim 13 wherein said compound is E-3-{1-[2-methyl-3-(3-pyridylmethyl)]indolyl} acrylic acid.

* * * * *